United States Patent [19]

Barthole et al.

[11] Patent Number: 4,990,441

[45] Date of Patent: Feb. 5, 1991

[54] PROCESS FOR SEPARATING 2-KETO-L-GULONIC ACID FROM A FERMENTED MEDIUM

[75] Inventors: Jean-Pierre Barthole, Elbeuf; Jean Filippi, Le Peage de Roussillon; Aurelia Jaeger-Seddik, Paris; Isidore Le Fur, Thiais; Jean-Yves Pommier, Paris, all of France

[73] Assignee: Rhone-Poulenc Sante, Antony, France

[21] Appl. No.: 405,126

[22] Filed: Sep. 11, 1989

[30] Foreign Application Priority Data

Sep. 13, 1988 [FR] France .................................. 88 11902

[51] Int. Cl.$^5$ ........................ C12P 7/60; C07C 51/42; C07C 59/347
[52] U.S. Cl. ................................... 435/138; 435/280; 435/317.1; 435/803
[58] Field of Search ............. 435/138, 280, 803, 317.1

[56] References Cited

U.S. PATENT DOCUMENTS 2,539,472 1/1951 Ratchford .
3,963,574 6/1976 Sonoyama .
4,421,924 12/1983 Crawford ........................... 562/587

FOREIGN PATENT DOCUMENTS 0213591 3/1987 European Pat. Off. .
0221707 5/1987 European Pat. Off. .

*Primary Examiner*—Herbert J. Lilling
*Attorney, Agent, or Firm*—Morgan & Finnegan

[57] ABSTRACT

2-Keto-L-gulonic acid is separated from a fermented medium containing the calcium salt of 2-keto-L-gulonic acid, by carrying out the following operations: separation of insolubles; removal of inorganic cations; and separation of the 2-keto-L-gulonic acid.

1 Claim, No Drawings

PROCESS FOR SEPARATING 2-KETO-L-GULONIC ACID FROM A FERMENTED MEDIUM

This invention relates to the separation of 2-keto-L-gulonic acid from a fermented medium.

2-Keto-L-gulonic acid, which is an intermediate in the synthesis of ascorbic acid, is generally produced in the form of calcium 2-keto-L-gulonate in media fermented by appropriate microorganisms.

To convert it into ascorbic acid, it is particularly advantageous to be able to use the 2-keto-L-gulonic acid either in the free form (2KLG-H) or in the form of the sodium salt (2KLG-Na), and, in either case, in a form which is as pure as possible.

According to Japanese Patent Application Nos. JP 52.66684 and JP 53.62894, it is known to prepare practically pure sodium 2-keto-L-gulonate from a fermented medium containing calcium 2-keto-L-gulonate. However, industrial implementation of these processes does not allow the 2-keto-L-gulonic acid which is required for later conversion into ascorbic acid to be obtained directly.

It has now been found, and it is this which forms the subject of the present invention, that practically pure 2-keto-L-gulonic acid (2KLG-H) can be obtained in good yields from fermented media containing calcium 2-keto-L-gulonate by a simple and easily reproducible process.

The fermented media generally contain, besides the 2-keto-L-gulonic acid in the form of the calcium salt, an insoluble biomass and organic and inorganic impurities, the inorganic impurities consisting essentially of inorganic anions associated with metallic cations such as sodium, potassium or magnesium ions.

The process of the invention essentially comprises the following stages:
(1) separating insolubles from the fermented medium;
(2) demineralizing (i.e. removing inorganic cations from) the medium; and
(3) separating the 2-keto-L-gulonic acid.

The process can be implemented continuously or discontinuously.

The biomass and the other insoluble substances, which generally represent from 1.5 to 3% by weight of the entire medium, can be separated from the medium:
either by centrifugation, preferably after flocculation with a flocculating agent such as, for example, an agent of the polyacrylamide type;
or by filtration, preferably under reduced pressure, after flocculation with a flocculating agent such as, for example, a polyacrylamide, and addition of a filtration additive such as, for example, wood flour or diatomaceous earth,
or by ultrafiltration across an appropriate inorganic or organic membrane such as a polyvinylidenedifluoride membrane or a membrane of $ZrO_2$ on a carbon matrix.

The medium from which the biomass and the other insoluble substances have been removed can be concentrated, either by evaporation under reduced pressure at a temperature of less than 60° C. to a volume corresponding to between ¼ and ⅓ of the initial volume, or by reverse osmosis on a polysulphone membrane at a temperature of about 50° C. until it reaches about half its volume.

The concentrated medium is generally acidified by addition of concentrated sulphuric acid in a practically stoichiometric quantity with respect to the calcium present, at a temperature less than or equal to 40° C. The calcium sulphate which precipitates is separated by filtration and washed with water. The filtrate, which contains various cations, the principal of which are the unprecipitated calcium and sodium, potassium and magnesium cations, is decationized and acidified by contact with a cation-exchange resin, preferably by passage through a column of polymeric cation-exchange resin, preferably of the sulphone type, in the acid (hydrogen) form.

It is also possible, before concentration, to decationize and acidify the medium by direct passage over a cationic resin, preferably of the sulphone type, in the acid form.

The medium from which the sediments and the cations have been removed, optionally concentrated, can then be treated to remove anions of strong inorganic acids in solution by contact with a weekly basic anion-exchange resin e.g. by passage over a polymeric anion-exchange resin, preferably of the dialkylamino type, in the basic (hydroxyl) form.

The demineralized solution is then preferably concentrated by evaporation under reduced pressure at a temperature less than 60° C. to about 70% of the initial volume. Crystallization of the 2-keto-L-gulonic acid is obtained by an additional concentration under reduced pressure at a temperature of about 40° C. until reduction of the volume of between about 30 and 40%, optionally followed by cooling of the crystal slurry.

It can be particularly advantageous to carry out crystallization continuously, in a crystallizer functioning by evaporation under reduced pressure at a temperature of about 40° C. and provided with an external exchanger. The crystals obtained are separated by filtration and by centrifugation and then washed with water. The 2-keto-L-gulonic acid is isolated in the form of a monohydrate the purity of which is generally about 100%. The molecule of water of hydration can be removed by heating under reduced pressure.

Generally drying of the wet monohydrated 2-keto-L-gulonic acid crystals is carried out by transporting them under a flow of warm air.

According to a feature of the present invention, 2-keto-L-gulonic acid can also be obtained by extraction of the concentrated and demineralized medium with a suitable organic solvent which is an optionally halogenated aliphatic or aromatic hydrocarbon containing in solution an aliphatic amine, preferably secondary, containing more than 20 carbon atoms. The organic solution thus obtained can be extracted with an aqueous solution of a strong inorganic acid chosen from hydrochloric, sulphuric or nitric acids, the concentration of which can be between 0.5 N and 3 N. The aqueous solution thus obtained can then be concentrated to dryness to give monohydrated 2-keto-L-gulonic acid in the powder form, the purity of which is generally greater than 90%.

The following Examples illustrate the invention.

EXAMPLE 1

Separation of the insolubles from the fermented medium

A fermented medium, obtained by culture of a strain of Corynebacterium which produces 2-keto-L-gulonic acid, containing about 1.6% of biomass and other insoluble substances and 10% of calcium 2-keto-L-gulonate is used.

The biomass and other insoluble substances can be separated by one of the following methods:

(1) Fermented medium (123 kg) containing sediments (about 2 kg) is passed across a Carbosep ultrafiltration membrane, the porosity of which is 80,000 Da, at a temperature of 40° C. A permeate (112 kg) free of insoluble products and a retentate (11 kg) containing the whole of the sediments and in which the concentration of calcium 2-keto-L-gulonate is equal to that in the permeate, is thus obtained.

The retentate is exhausted by diafiltration, by successive additions of water to the retentate in the course of an ultrafiltration which is identical to that described above. Diafiltration is stopped when the content of calcium 2-keto-L-gulonate in the pooled permeates corresponds to a recovery level of at least 99%.

(2) An aqueous 5 g/liter solution (20 cc) of a polyacrylamide-type flocculating agent Floerger 8850 is added to whole medium (500 g), stirred vigorously. After a few minutes of contact, wood flour (10 g) is added while maintaining vigorous stirring. The mixture obtained is filtered through filter cloth under reduced pressure (300 mm Hg; 40 kPa). The filter cake is washed with water (50 cc).

The loss of calcium 2-keto-L-gulonate is less than 2%. The weight of the filtrate containing 9.4% of calcium 2-keto-L-gulonate is 520 g.

(3) Whole medium (200 liters) containing 2.7% sediment is flocculated with the aid of a 5 g/liter aqueous solution (8 liters) of a polyacrylamide-type flocculating agent (Floerger 8850) and then continuously introduced at a flow rate of 2000 liters/hour into a plate-centrifuge clarifier of 7200 $m^2$ equivalent surface area. A clarified medium containing 0.1% of sediments is recovered.

EXAMPLE 2

Concentration of the medium

The medium from which the insolubles have been removed can be concentrated according to one of the following methods:

(1) Insolubles-free medium (225 liters) is concentrated by evaporation under reduced pressure (72 mm Hg; 9.5 kPa) at a temperature of 47° C. to a volume of 62 liters. Thermal degradation is less than 0.5%.

(2) Insolubles-free medium (60 liters) is concentrated by passage through a reverse osmosis module equipped with polysulphone membranes (PCI Z 99) at a flow rate of 25 liters/h.$m^2$ and at a temperature less than or equal to 50° C., until a volume of 30 liters is obtained.

EXAMPLE 3

Precipitation of calcium sulphate

To a stirred reactor, maintained at a temperature less than or equal to 40° C. and containing concentrated medium (2 liters) obtained under the conditions described in Example 2 1), is added a quantity of concentrated sulphuric acid, that is 100 cc, which corresponds, in moles, to the total quantity of calcium present in the medium. The calcium sulphate which precipitates in the form of the dihydrate is separated by filtration and washed with water. The filtrate and the pooled washings contain 99.5 mol % of the initial 2-keto-L-gulonic acid. The yield of the calcium removal is 95%.

EXAMPLE 4

Removal of cations 3 liters of the filtrate obtained in Example 3 (before being mixed with the water from washing the calcium sulphate cake) are passed through a column 80 cm high and 5 cm in diameter containing strong cationic resin (1.6 liter; Amberlite IRC 120) in the hydrogen form.

After washing, medium (5.5 liters), is obtained in which the content of sulphate solids is less than 1% with respect to the 2-keto-L-gulonic acid present in the medium. The recovery level of the 2-keto-L-gulonic acid is greater than 99.5%.

EXAMPLE 5

Removal of the anions

The medium obtained in Example 4 (0.4 liter) is passed through a column 10 cm high and 1.4 cm in diameter containing weak anion-exchange resin (15 cc; Amberlite IRA 93) in the hydroxyl form in order to reduce the sulphuric acid content in the acidified medium by a factor of 10. The loss of 2-keto-L-gulonic acid does not exceed 2% of the quantity introduced.

EXAMPLE 6

Crystallization of 2-keto-L-gulonic acid

Medium obtained under the conditions of Example 5 (5000 g) is concentrated by evaporation to obtain a solution (3430 g) containing 2-keto-L-gulonic acid (1170 g) and impurities (255 g). The concentrate thus obtained is partially concentrated under reduced pressure (40 mm Hg; 5.3 kPa) at a temperature of 40° C. until it reaches a weight of 2010 g. This additional concentration leads to crystallization of hydrated 2-keto-L-gulonic acid. The slurry of crystals is cooled to 25° C. The crystals are separated by filtration and washed with water. Hydrated 2-keto-L-gulonic acid (930 g) is thus obtained, the purity of which is greater than 99%, and the content of sulphate solids of which is less than 0.1% The yield is 73%.

The filtration mother liquors and the washing waters are pooled and then concentrated under reduced pressure (40 mm Hg; 5.3 kPa) to a weight of 710 g. After cooling, the crystals are separated by filtration and washed with water. Monohydrated 2-keto-L-gulonic acid (285 g) is thus obtained, the purity of which is 89%

The wet (5.8% water) crystals of 2-keto-L-gulonic acid monohydrate, the purity of which is greater than 99% (9400 g) are dried with air at 75° C. circulating a 5 m/s in a pneumatic transport drier, the dwell time being 3 seconds. Monohydrated 2-keto-L-gulonic acid (8850 g) is thus obtained. It can be dehydrated by heating to 40° C. under reduced pressure (5 mm Hg; 0.6 kPa) for several hours.

EXAMPLE 7

Medium (1 liter) from which the sediments and the cations have been removed, containing 2-keto-L-gulonic acid (80 g) having a purity of 84% is put in contact with a solution (1 liter) of Adogen 83 (registered trademark of Schering; 260 g) in kerosene for 0.5 hour at 50° C. The 2-keto-L-gulonic acid (83%) which is extracted in the organic phase is quantitatively re extracted with a 1 N aqueous solution of nitric acid (690 cc).

The solution, after concentration to dryness, provides a crystallized product (81.5 g) containing monohydrated 2-keto-L-gulonic acid (89%).

We claim:

1. A process for separating 2-keto-L-gulonic acid from a fermented medium containing the calcium salt of 2-keto-L-gulonic acid which comprises separating the insolubles from the fermented medium by ultrafiltration, filtration in the presence of a flocculating agent and a filtration additive, or centrifugation in the presence of a flocculating agent, concentrating the medium obtained by evaporation under reduced pressure or by reverse osmosis, removing inorganic cations from the concentrated medium by adding to the said medium substantially the stoichiometric quantity of sulphuric acid to precipitate most of the calcium sulphate, removing calcium sulphate and then contacting the said medium with a cation-exchange resin in the hydrogen form, then removing residual strong acid anions by contact with an anion-exchange resin in the hydroxyl form, and then concentrating the medium under reduced pressure and allowing the 2-keto-L-gulonic acid to crystallize out or extracting the 2-keto-L-gulonic acid from the medium with a hydrocarbon solvent having an aliphatic amine of more than 20 carbon atoms dissolved therein, and then re-extracting into an aqueous solution of hydrochloric acid or nitric acid or sulphuric acid, and then isolating the 2-keto-L-gulonic acid by evaporating of the aqueous extract.

* * * * *